United States Patent [19]
Chu et al.

[11] Patent Number: 5,447,845
[45] Date of Patent: Sep. 5, 1995

[54] ANALYTE-RESPONSIVE KTP COMPOSITION AND METHOD

[75] Inventors: David K. Chu; Richard C. Ebersole, both of Wilmington; Hui Hsiung, Hockessin, all of Del.

[73] Assignee: E. I. Du Pont de Nemours and Company, Wilmington, Del.

[21] Appl. No.: 348,585

[22] Filed: Dec. 6, 1994

Related U.S. Application Data

[63] Continuation of Ser. No. 69,906, Jun. 1, 1993, abandoned.

[51] Int. Cl.$^6$ .................. G01N 33/543; G01N 33/551
[52] U.S. Cl. .......................................... 435/6; 73/587; 73/590; 310/311; 310/313 R; 310/313 B; 310/340; 356/369; 385/130; 422/55; 422/57; 422/82.01; 422/82.05; 435/808; 435/970; 436/518; 436/524; 436/525; 436/527
[58] Field of Search .................. 73/587, 590, DIG. 4; 310/311, 313 R, 313 B, 340; 356/364, 369; 385/130; 422/55, 57, 82.01, 82.05; 435/6, 808, 970; 436/164, 518, 524, 525, 527, 532, 805–807

[56] References Cited

U.S. PATENT DOCUMENTS

| | | | |
|---|---|---|---|
| 3,949,323 | 4/1976 | Bierlein et al. | 332/7.51 |
| 4,231,838 | 11/1980 | Gier | 156/600 |
| 4,236,893 | 12/1980 | Rice | 23/230 |
| 4,305,778 | 12/1981 | Gier | 156/623 |
| 4,314,821 | 2/1982 | Rice | 23/230 |
| 4,735,906 | 4/1988 | Bastiaans | 436/527 |
| 4,767,719 | 8/1988 | Finlan | 422/82.05 |
| 4,789,804 | 12/1988 | Karube et al. | 310/311 |
| 4,847,193 | 7/1989 | Richards et al. | 435/6 |
| 5,001,053 | 3/1991 | Takahashi et al. | 422/82.01 |
| 5,077,210 | 12/1991 | Eigler et al. | 435/176 |

FOREIGN PATENT DOCUMENTS

| | | | |
|---|---|---|---|
| 0215669 | 3/1987 | European Pat. Off. | H01L 41/08 |
| 0261642 | 3/1988 | European Pat. Off. | G01N 21/75 |
| 0453224 | 10/1991 | European Pat. Off. | G01N 33/543 |

OTHER PUBLICATIONS

Buritskii, K. S. et al., *Electronic Letters*, 27(21), 1896–1897.
Chu, D. K. T. et al., *Proc. IEEE Freq. Control Symp.*, 46, 732–743 (1992).
G. Harrison et al., *Methods of Experimental Physics*, 19(3):137–171.
H. Wholtjen, *Sensors and Actuators*, 5:307–324 (1984).
Y. A. Kosevich, et al., *Sov. Phys. Acoust.*, 36(1):28–30 (Jan./Feb. 1990).
P. Kielczynski, et al., *J. Acoust. Soc. Am.*, 86(2):818–827 (Aug. 1989).
A. J. Ricco, et al., *Appl. Phys. Lett.*, 50(21):1474 (1987).
S. A. Barker, *Biosensors–Fundamentals and Applications*, pp. 85–98 (1987).
H. B. Serreze et al., *Rev. Sci. Instrum.*, 45:1613–1614 (1974).
B. A. Auld, *Acous. Fields and Waves in Solids*, 2(12):271–281 (1973).
E. S. Grabbe et al., *J. Electronal. Chem.*, 223:67–78 (1987).
J. N. Ngwainbi et al., *J. Am. Chem. Soc.*, 108:5444–5447 (1986).
A. Shons et al., *J. Biomed. Mater. Res.*, 6:565–570 (1972).
J. E. Roederer et al., *Anal. Chem.*, 55(14):2333–2336 (Dec. 1983).

*Primary Examiner*—Toni R. Scheiner
*Assistant Examiner*—Christopher L. Chin

[57] ABSTRACT

This invention relates to analyte-responsive compositions and analyte detection methods using these compositions, and, more particularly, to such compositions based on potassium titanyl phosphate (KTP) and analogs thereof and to analyte detection methods based on piezoelectric and optical properties of materials.

15 Claims, 3 Drawing Sheets

ANALYTE-RESPONSIVE KTP COMPOSITION AND METHOD

This is a continuation of application Ser. No. 08/069,906, filed Jun. 1, 1993, now abandoned.

FIELD OF THE INVENTION

This invention relates to analyte-responsive compositions and analyte detection methods using these compositions, and, more particularly, to such compositions based on potassium titanyl phosphate and analogs thereof.

BACKGROUND OF THE INVENTION

A variety of detection methods have been developed in the art to detect chemical and biological substances in the nanomolar range, and such methods are finding increasing utility in analytical applications ranging from health care to waste treatment. One such general method is based on piezoelectric substances, commonly known as piezoelectric transducers, and, to a lesser extent, optical substances. Typical optical methods for detecting components of biological systems are described in European Patent Publication 0 261 642. Typical piezoelectric methods are described in U.S. Pat. Nos. 4,236,893, 4,314,821, and European Patent Publication 0 215 669.

The ability of piezoelectric transducers to detect small changes in mass, viscosity and density at their surfaces has made them particularly useful as analytical tools where the measurement of very small amounts of material must be made in solution. A typical piezoelectric transducer, based on quartz, comprising an AT-cut quartz crystal sandwiched between two metal excitation electrodes, is described in Karube et al. U.S. Pat. No. 4,789,804. In accordance with this patent, the concentration of an analyte in solution was calculated on the basis of the change in resonance frequency of a bulk shear acoustic wave generated therein caused by the weight of an analyte added to a receptor material immobilized on the surface of the quartz-based device.

Although a useful tool in solution environments, conventional piezoelectric and/or optical substances must undergo considerable complex surface modification to provide specificity for the analyte to be detected. In cases where the analytes to be detected are biological in nature, bioreceptor agents (antigens, antibodies or other ligands) must be immobilized somehow on the surface of the piezoelectric substance. Because attachment of such receptor agents directly to the surface of commonly used piezoelectric substances, e.g., quartz, has been found to be generally unsuccessful, a variety of surface modifications have been developed to facilitate immobilization of receptors. One method of surface modification involves the use of silane and heterobifunctional crosslinking agents, e.g., Eigler et al. U.S. Pat. No. 5,077,210.

Piezoelectric transducers utilized for types of liquid analyses, such as viscosity measurement of an unknown material, involve the generation and propagation of a bulk shear acoustic wave into the unknown material, usually a liquid, see, for example, G. Harrison et al., "Methods of Experimental Physics" Volume 19, Chapter 3, pages 137–171. Due to the low frequency of the bulk shear acoustic wave and large propagation losses in the liquid, the sensitivity of the measurement is limited. Recently, surface elastic waves such as Rayleigh, Bleustein-Gulyaev, and Love waves have been used to sense (measure) parameters of a overlay thin film (liquid) because of the higher sensitivity of the measurement using such waves, see, for example, Hank Wohltjen, Sensors and Actuators, 5, 307–324, 1984; Yu A. Kosevich and E. S. Syrkin, Sov. Phys. Acoust. 36 (1), 8–30, January–February 1990; P. Kielczynski and R. Plowiec, J. Acoust. Soc. AM. 86(2), 818–827, August 1989. Although surface acoustic waves (SAW) possess high sensitivities to the vapor phase sensing applications, they are not adequate for liquid sensing applications, such as biosensing and viscosity measurements, because of large radiation losses to the overlay liquid. See, for example, A. J. Ricco and S. J. Martin, Appl. Phys. Lett, 50(21), 1474 (1987). Therefore, in addition to the SAW waves, it is important to have shear modes available which do not suffer large radiation loss into the liquid so that complete mechanical properties such as elastic modules and viscosity of the overlay material can be obtained. It is a tremendous advantage for a material being able to support surface elastic modes which contains the desired particle velocity components for measurement and sensing applications.

This invention provides a composition that is particularly useful for applications such as biological immunosensing or polymeric viscosity sensing, based upon acoustic or optical changes in the composition.

SUMMARY OF THE INVENTION

This invention is directed to a composition of matter comprising crystalline $MTiOXO_4$, wherein M is selected from the group consisting of K, Rb, Tl and $NH_4$, and X is selected from the group consisting of P and As, wherein the crystalline $MTiOXO_4$ has an analyte receptor immobilized on the surface thereof. The receptor may be immobilized directly to the surface of the crystalline $MTiOXO_4$, or alternatively, immobilized to the crystalline $MTiOXO_4$ through an immobilization matrix. The analyte receptor may be biological, for the detection of biological analytes such as, for example hormones, microbes, cells, immunoglobulins, enzymes, proteins, or nucleic acids; or the analyte receptor may be nonbiological, for the detection, for example, of specific chemicals, polymers, or particulates.

This invention also provides a process for the detection of an analyte, comprising the steps of:
(a) immobilizing onto the surface of crystalline $MTiOXO_4$ a receptor having the ability to bind the analyte,
  wherein M is selected from the group consisting of K, Rb, Tl, $NH_4$; and X is P or As;
(b) contacting the surface of the crystalline $MTiOXO_4$ with a solution containing the analyte to be detected, whereby the analyte will bind to the immobilized receptor;
(c) applying electromagnetic energy to the crystalline $MTiOXO_4$, whereby acoustic waves are generated; and
(d) measuring the frequency of the acoustic waves;
  whereby by detecting a change in the frequency of said waves the presence of analyte is detected.

This invention also provides a method for the detection of an analyte, comprising the steps of:
(a) immobilizing onto the surface of crystalline $MTiOXO_4$ a receptor having the ability to bind the analyte,
  wherein M is selected from the group consisting of K, Rb, Tl, $NH_4$; and X is P or As;

(b) contacting the surface of the crystalline MTiOXO$_4$ with a solution containing the analyte to be detected, whereby the analyte will bind to the immobilized receptor;

(c) applying electromagnetic radiation (light) to the crystalline MTiOXO$_4$; and (d) measuring the optical properties of the MTiOXO$_4$;

whereby by detecting a change in said optical properties the presence of analyte is detected.

In both processes of the invention the analyte to be detected may be biological or nonbiological, and may be immobilized directly to the crystalline MTiOXO$_4$ or indirectly through an immobilization matrix.

This invention is based on the discovery that crystalline MTiOXO$_4$, particularly where M=K and X=P (referred to as KTP), have the desired properties to generate surface acoustic waves (Rayleigh or SAWs) in a z-cut plate and Bleustein-Gulyaev waves (BGs) in a y (or x) cut plate. Since SAWs have the particle velocity components in sagittal plane and BGs have the particle velocity component in the direction perpendicular to the sagittal plane, therefore, KTP exhibits the necessary properties to satisfy the requirements on particle velocity components for sensing and measurement applications. The optical properties of crystalline MTiOXO$_4$ are well known in the art, see, for example, Bierlein et al. U.S. Pat. No. 3,949,323. Furthermore, Applicants have discovered that crystalline MTiOXO$_4$ can immobilize an analyte receptor on the surface thereof.

DETAILED DESCRIPTION OF THE INVENTION

Figure 1:
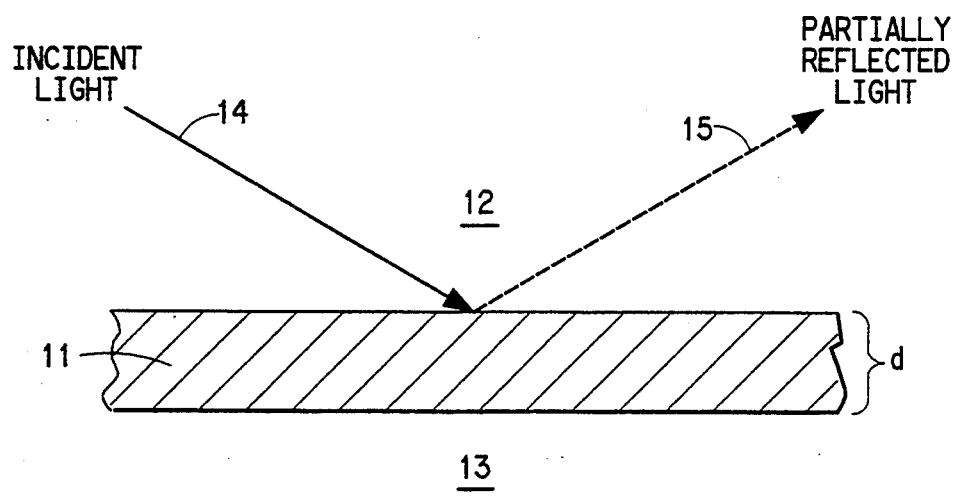
FIG. 1 is a schematic view of crystalline MTiOXO$_4$ surrounded by media having different optical constants.

Crystalline MTiOXO$_4$ useful in the practice of this invention can be prepared by a variety of methods well known in the art. Two most common methods are referred to as hydrothermal and flux, as described in U.S. Pat. Nos. 4,305,778 and 4,231,838, respectively. It is preferred that the crystalline MTiOXO$_4$ be in the form of a single crystal or a thin film, but no special surface preparation is necessary outside the standard polishing operation that is normally done after crystal growth. Of the many MTiOXO$_4$ analogues, KTiOPO$_4$ is preferred. The crystalline substrate can be in the form of a single crystal or crystalline thin film. In use the crystalline substrate can be cut along the x-, y- or z-axis. All rotated cuts will work for the generation of SAW except x- and y- principle cut, but crystals cut along the x- or y-axis are used for the generation of Bleustein-Gulyaev waves. Bulk crystalline substrates at MTiOXO$_4$ such as KTP may be used for generating acoustic waves having a wavelength equal to that of the period of IDT (interdigital transducer) used for acoustic wave generation.

The analyte receptor immobilized on the surface of the crystalline MTiOXO$_4$ is intended to include both biologically active receptors, commonly called bioreceptors, and non-biologically active receptors, such as chemicals, particles, and polymeric materials. However, the greatest advantages of this invention are realized when bioreceptors are employed for the detection of biological analytes. Bioreceptors suitable for the practice of this invention are one member of an analyte-specific binding pair. Commonly, they are of two types, immunoreactive or non-immunoreactive bioreceptors.

Immune specific bioreceptor/bioanalyte are exemplified by antigen/antibody systems or Hapten/antibody systems. The antibody member, whether polyclonal, monoclonal, or an immunoreactive fragment thereof can be produced by methods well known in the art, e.g., Richards et al. U.S. Pat. No. 4,847,193. The term immunoreactive antibody fragment or immunoreactive fragment means a part or fragment of immunoreactive antibody or substance which contain the binding region of the antibody or substance. Such fragments may be of the Fab-type, which are fragments devoid of the Fc portion, e.g., Fab, Fab' and F(ab')2 fragments or the so-called "half-molecule" fragment produced by reductive cleavage of the disulfide bonds connecting the heavy chain components of the intact antibody. If the antigen member of the binding bioreceptor is not immunogenic, e.g., a hapten, it can be covalently coupled to a carrier protein to render it immunogenic. Alternatively, the bioreceptor could be the "antigen" or a surrogate of the antigen, which would be capable of binding its "bioreceptor" as the other member of the bindng pair.

Non-immunoreactive bioreceptors are derived from binding pairs which share a natural affinity for each other, but are not antibodies. Generally these bioreceptors can be derived from lectins, binding proteins or chelating agents. Examples of non-immune binding pairs are biotin/avidin or biotin/streptavidin, folic acid/folate binding protein, complementary oligonucleotides, nucleic acids, complementary DNA or RNA. The nucleic acids can be isolated from natural sources or produced synthetically by methods well known in the art. Other types of bioreceptors include enzymes and cofactors, cells, microorganisms, organelles, tissue sections, liposomes, and hormones. Typical analytes specific to these receptors include nucleic acids, proteins, hormones, microorganisms, cells, enzymes, hormones, etc., from environmental, veterinary, and human fluid samples.

Generally, the prior art in the field of analyte detection via optical or piezoelectric sensing has relied upon crystal surfaces, usually quartz, which of necessity have been modified by priming, coating, or binding reagent layers, or combinations thereof, to immobilize the analyte receptor. Typical examples of such layers include gold, heterobifunctional reagents, polymeric films such as styrene, and silane reagents. The present invention is unique in that it is the first to utilize potassium titanyl phosphate (KTP) crystals in piezoelectric and optical analyte detection methods, and surprisingly, Applicants have discovered that in such utility the KTP crystals can bind the analyte receptors directly. In some instances, this bypasses the need for surface modification. Alternatively, the bioreceptors, or nonbiological receptors of the invention can be immobilized indirectly by a variety of procedures well known in the art. A review of conventional methods is found in A. P. F. Turner et al., "Biosensors-Fundamentals and Applications", Oxford Science Publications, pages 85–98 (1987), which is incorporated by reference herein. This reference demonstrates several methods well known in this art for immobilization of biological analytes through a matrix, including surface treatments of the substrate with: titanium tetrachloride; ferrocene; a gel matrix such as alginate and gelatin; glutaraldehyde and hexamethylenediamine; alumina; lipase; charcoal; clay; cellulose; kaolinite; silica; hydroxyapitite; collagen; and polyacrylamide; to immobilize various biological analytes.

Potassium titanyl phosphate (KTP) and analogs are recognized as having a variety of optical characteristics and piezoelectric properties which render them useful in optical storage/transmission applications as well as frequency control devices via the use of KTP as the optical or piezoelectric element combined with optical sensings apparatus or frequency sensing apparatus.

Examples of typical uses of the piezoelectric properties of KTP to generate and control frequency are described in copending, commmonly assigned application Ser. No. 07/924,691. The apparatus described therein can be utilized to practice the analytical processes of this invention. In the uses described therein the crystalline substrate may be used for generating acoustic waves having a wavelength equal to about the period of the interdigital transducer (IDT) used for acoustic wave generation. Surface-modified crystalline substrate having periodic domain reversals may be used for generating acoustic waves having a wavelength equal to about one-half of the period of the IDT used for acoustic wave generation. The types of waves generated in the crystalline substrate are fundamentally determined by crystal structure. The SAW generated in the crystalline substrates travel through the substrate at rates of about 3600 meters per second; SSBAW, 6000 meters per second; and bulk acoustic waves, 7800 meters per second. SAW can be generated directly on a z-cut $MTiOXO_4$ substrate without any ionic dopants such as rubidium. B-G waves can also be generated on x or y cut substrate with propagation along z axis. There are several advantages of using $MTiOXO_4$ for generating B-G waves. First, since they are bulk acoustic waves, the bulk coupling coefficient (which is a material index of how efficient the material can convert the electrical energy into acoustic energy) of B-G waves can be very high (roughly about 20%, or about forty times the surface coupling coefficient of quartz).

In practice interdigital transducers (IDT) can be deposited on the surface of the crystalline substrate by conventional lithographic techniques. To develop the desired pattern onto $MTiOXO_4$ substrate one may use the following steps: (1) prepare the $MTiOXO_4$ substrate (usually z-cut for SAWs or x- or y-cut for B-G waves); (2) polish the substrate to provide a flatness better than a half optical wavelength (typically about 0.3 μm flatness variation); (3) evaporate a conductive material, typically a metal film such as titanium about 1000 Å thick, onto the crystalline substrate using an electron beam evaporator; (4) spin a positive photoresist (e.g., a photopolymer) onto the substrate and softbake (prebake) at a suitable temperature and time period for the photoresist used; (5) align a predesigned photomask and expose it to light for a time sufficient to develop the desired resolution; (6) hardbake (postbake) for a suitable time and temperature for the photoresist used; (7) develop the exposed photoresist using a suitable developer; (8) etch the titanium off the area which has no photoresist cover; and (9) strip off unexposed photoresist using specified stripper (e.g., acetone). After all these processing steps, one can use a commercially available network analyzer such as Hewlett-Packard 8753C to analyze the performance of the devices. The pattern chosen for the IDT determines how the frequency is controlled. The operating frequency of an acoustic wave device is determined by the following equation:

$$f = v/\lambda$$

where v is the velocity of the acoustic wave generated in the device by the IDT and λ is the wavelength of the acoustic wave generated in the device by the IDT. Conventionally, the wavelength of the acoustic wave is determined by the IDT pattern. The smaller the width of the IDT "finger" in the direction of wave propagation, the smaller the wavelength of the acoustic wave generated in the device by the IDT, or the higher the operating frequency. However, there is a practical limit as to how small one can make the width of the IDT fingers due to the diffraction-free limit of the exposing sources such as UV light, electronic beam or X-ray.

Figure 2:
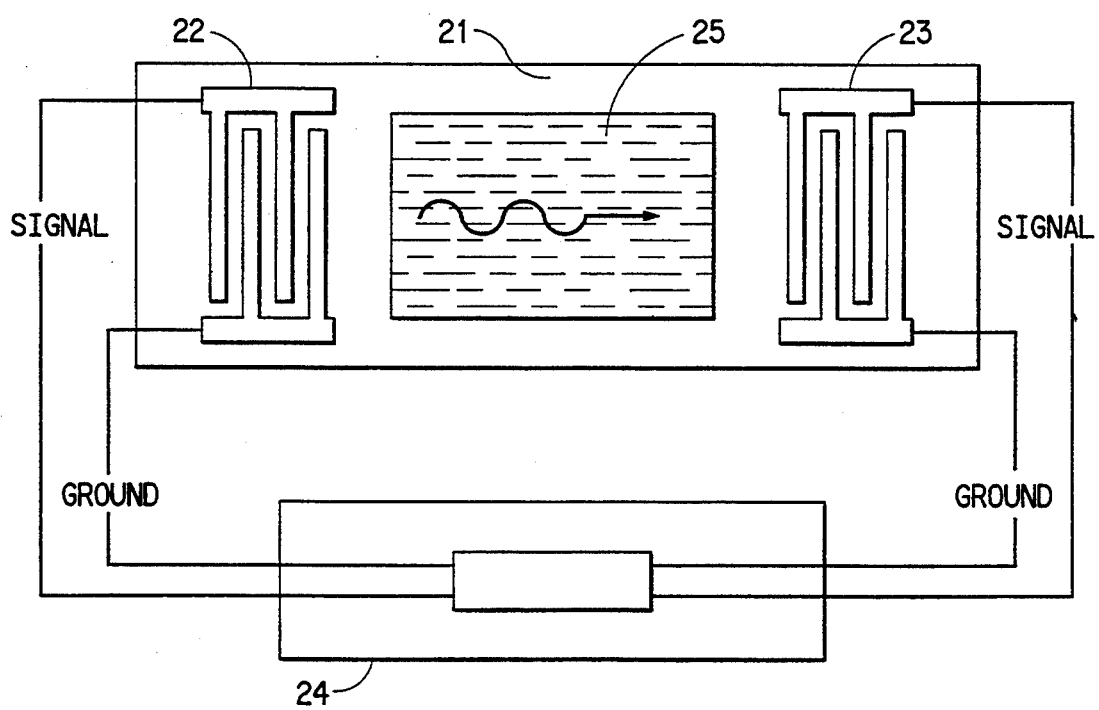
FIG. 2 is a schematic view of acoustic wave generation/sensing system useful in the practice of this invention.

Referring to FIG. 2, a typical piezoelectric device useful for the practice of the process of this invention comprises a crystalline $MTiOXO_4$, 21, onto which are deposited IDTs, 22 and 23, which generate acoustic waves in crystalline $MTiOXO_4$, 21. IDTs, 22 and 23 are electrically connected to an electric signal responsive device, 24, e.g., a network analyzer, which provides the frequency response between the two IDTs before and after application of an analyte substance, 25, e.g., a liquid whose viscosity is to be determined.

A wide variety of optical sensing apparati, including those employed in waveguide and nonlinear optical modes, can be utilized to sense the change in optical properties of crystalline $MTiOXO_4$ resulting from changes on its surface. One preferred method, ellipsometry, is described in Example 1 below. Other preferred modes include nonlinear optical and waveguide applications.

Without further elaboration, it is believed that one skilled in the art can, using the preceding description, utilize the present invention to its fullest extent. The following specific embodiments are, therefore, to be construed as merely illustrative, and not limiting of the disclosure in any way whatsoever.

EXAMPLES

EXAMPLE 1

Ellipsometry Sensing of Biomolecules using the Surface of Crystalline KTP

In this example, Applicants demonstrate the use of ellipsometry for probing binding processes of certain proteins at $KTiOPO_4$ (KTP) surfaces. The demonstration involves first the binding of an antibody via direct adsorption to a KTP surface forming an antibody monolayer at the surface, followed by selective binding of the corresponding antigen to the antibody monolayer—the latter known as an immuno process. This Example shows that the advantage of using KTP surfaces in such an application is two-fold: First, the binding of antibody molecules to KTP surfaces is direct. Other than a simple cleaning procedure, no additional treatments of the surfaces are required. Second, KTP has a relatively high optical constant, which enhances the sensitivity of the ellipsometry detection.

Ellipsometry is an optical technique commonly used for determining thickness or optical constants of thin films. The technique is illustrated with reference to FIG. 1. Consider a thin film, 11, of optical constant $\epsilon_f$ and thickness d, surrounded by two media, 12 and 13, of optical constants $\epsilon_1$ and $\epsilon_2$, respectively, as shown in FIG. 1. When a linearly polarized laser light, 14, of wavelength $\lambda$ is directed at the thin-film, 11, incorporated interface, the reflected light, 15, becomes elliptically polarized. The degree of ellipticity is determined by a measurable quantity known as "phase retardation", $\Delta$. In the limit $d<<\lambda$, $\Delta$ can be expressed as $$\Delta = 4\pi\lambda^{-1} F(\epsilon_1, \epsilon_2, \theta) \epsilon_f^{-1} (\epsilon_f - \epsilon_1)(\epsilon_f - \epsilon_2) d, \quad (1)$$

where $F(\epsilon_1, \epsilon_2, \theta)$ is a coefficient dependent of $\epsilon_1$, $\epsilon_2$, and the light incident angle $\theta$. Equation (1) shows that the sensitivity of ellipsometry depends not only on the properties of the thin film itself, but also on the optical constants of the surrounding media. In addition, a larger difference between $\epsilon_1$ and $\epsilon_2$ increases the light reflectivity at the interface, which in turn increases the ellipsometry detection sensitivity.

In this Example, the thin film of interest comprises only one or two monolayers of proteins. Medium 13 is the KTP crystal, and Medium 12 is an aqueous solution that contains a small concentration of the proteins. At $\lambda = 632.8$ nm, for example, $\epsilon_1 \cong 1.8$ for a dilute aqueous solution and $\epsilon_2 \cong 3.1$ to 3.5 for various KTP surfaces. Depending on the water content in the monolayer film, the effective optical constant $\epsilon_f$ of a protein monolayer at an aqueous-solid interface is in the range 1.8 to 2.4. Therefore, compared to a conventional protein-binding substrate such as polystyrene ($\epsilon_2 \cong 2.5$), KTP offers a larger value of ($\epsilon_f - \epsilon_2$), and a larger difference between $\epsilon_1$ and $\epsilon_2$, both yielding a higher ellipsometry detection sensitivity.

The ellipsometer used was a polarization-modulated system employing an intensity-stabilized He—Ne laser operated at 632.8 nm (Spectra-Physics Model 117A) as the light source. The polarization modulator was a photoelastic modulator (Hinds International, Model PEM-80I) operated at 50 kHz and at a peak-to-peak modulation amplitude of $\lambda/10$. The design of the ellipsometer used in this Example substantially follows that of H. B. Serreze and R. B. Goldner, Rev. Sci. Instrum., 45, 1613–1614 (1974). However, in order to facilitate the study of longer-term (i.e., hours) protein-binding processes, we improved the ellipsometer design by monitoring the baseline drift of the optical system. This was accomplished by adding a reference optical path that bypassed the sample cell. The modulated optical signals from the signal and the reference arms were separately converted into electrical signals by two photodiodes (EG & G, Model SGD-100A) and then demodulated by two lock-in amplifiers (EG & G Princeton Applied Research, Model 5301A). The outputs of the lock-in amplifiers were then fed to a computer (IBM, Model PS/2 70486) for further analysis. The sensitivity of our phase-retardation measurement was about 0.1 mrad.

The KTP substrate was a 11 mm $\times$ 10 mm $\times$ 1.5 mm crystal slab with two large surfaces parallel to the crystalline x-y plane. One surface was optically polished and used for the antibody binding; the other surface was roughened to prevent the light reflection from this surface from reaching the photo detector. To prepare the KTP surface, first the crystal slab was sequentially cleaned by a laboratory detergent (Alconox), acetone, and methanol. It was then ultrasonically cleaned in a mixture of $H_2SO_4$ and "Nochromix" (Godax Laboratories, Inc., 480 Canal Street, New York, N.Y. 10013) at 30° C. for about 15 minutes, followed by a thorough rinse with double-distilled and de-ionized water. The KTP slab, with its polished side facing up, was situated at the bottom of a small Teflon (PTFE) trough filled with an aqueous solution (described below). The incident laser beam was focused by a lens (focal length 20 cm) to a spot of about 200 $\mu$m in diameter at the KTP surface. The laser beam first entered the liquid through the air-liquid interface. It was then partially reflected from the liquid-KTP interface (the antibody-binding surface), and then transmitted back into the air for detection. The light transmitted through the top KTP surface was diffused by the bottom KTP surface due to scattering from the roughened surface, and hence this light was rejected by the detection system. The light incident angle was 69.5° at the air-liquid interface and 44.6° at the liquid-KTP interface.

The antibody used for Example was goat anti-rabbit IgG purchased from Jackson Immuno Research Lab, Inc.; the corresponding antigen, rabbit IgG, was purchased from Sigma Immuno Chemicals. Two aqueous solvents were used: (1) a high purity water prepared by double distillation followed by de-ionization (Millipore "Mill-Q" System), with an equilibrium pH of 5.6; (2) a phosphate-buffered saline (PBS) aqueous solution that contains 10 mM of $(Na)_3PO_4$, 120 mM of NaCl, and 2.7 mM of KCl (pH=7.4).

The baseline for the phase-retardation measurement was obtained with the KTP substrate in place and the trough filled with the purified water. For the binding of goat anti-rabbit IgG onto the KTP surface (known as an incubation process), the purified water was replaced with a 2 $\mu$g/ml (about $1.4 \times 10^{-8}$M) solution of the antibody in the purified water. In-situ monitoring of the binding process started immediately after the antibody solution was in place. During the first minutes the phase-retardation signal appeared to increase in roughly equal steps of about 2 mrad, suggesting that the adsorption process involved multiple molecular layers of the antibody. In about two hours, the signal reached a maximum of about 20 mrad, corresponding to about ten antibody monolayers. To facilitate the ensuing immuno process, the multilayer antibody film must be reduced to a single monolayer. This was accomplished by replacing the antibody aqueous solution with the PBS solution containing no antibodies, followed by a waiting period of about two hours during which the excess layers of antibody desorbed from the KTP surface into PBS. This process was repeated to obtain a monolayer film of antibody. Alternatively, we obtained the monolayer coating by terminating the adsorption process at the moment when the binding of the first monolayer was complete, which occurred within the first five minutes of incubation. In either the PBS solution or in water, the monolayer coating of goat anti-rabbit IgG on KTP was stable.

The immuno reaction of the antigen with the antibody monolayer was demonstrated by filling the sample trough with a 2 $\mu$g/ml (about $1.4 \times 10^{-8}$M) solution of rabbit IgG in PBS. The phase-retardation signal increased instantaneously and within several minutes reached a maximum value of about 5 mrad, which remained stable for many hours. The increased signal of 3 mrad corresponded to that of a bound antigen monolayer.

EXAMPLE 2

Generation of SAW and BG Waves in KTP and Determination of Mass Variation of a Liquid Using the apparatus schematically represented in FIG. 2 without liquid overlay, a z-cut flux-grown KTP was used to generate SAW propagating along the y-axis. A photomask was designed so that the dimensions of the IDT are as follows: 1250 μm in length (aperture), 4 μm finger width and 4 μm spacing between two IDT fingers. The conventional photolithographic technique was used to fabricate Ti IDT's onto KTP surface. HP 8753C network analyzer was used to analyze the performance of the SAW device. A wavelength of 16 μm surface acoustic wave was generated due to the design of the IDT's. The measured center frequency was about 246 MHz, corresponding to a SAW velocity of 3936 m/sec, which agrees well with a calculated predicted value of 3950 m/sec.

A y-cut flux-grown KTP was used in the manner described above to generate B-G waves propagating along the x-axis. IDTs having 4 μm finger spacing and 4 μm finger width were fabricated on the KTP surface to generate a B-G wavelength of 16 μm. The aperture of the IDTs was 1250 μm. The same fabricating technique as the SAW's in previously described case was used for the B-G wave device. The measured data from network analyzer exhibited a center frequency at 266 MHz corresponding to a B-G velocity of 4256 m/sec, which is in the theoretically predicted range of 4247 and 4330 m/sec.

A B-G wave oscillator was manufactured using photolithographic techniques described in previous cases. Two fifty pairs IDT's were placed at a 320 μm apart and a 30 Ti strips with 4 μm wide, 1250 μm long, and a 4 μm spacing between two strips was put next to each IDT. The frequency response of the tested device had the center frequency at about 264 MHz with a total loss about 44.7 dB. Then less than 5 μl of mineral oil was added between the two IDT to see how the frequency response of the device changed. The perturbed B-G device then exhibited a center frequency at 200 KHz lower than the unperturbed condition (determined above without the mineral oil) and the total loss was about 9 dB greater than the unperturbed condition. From the reduction in acoustic velocity (changes in center frequency) and the increase in total insertion loss, we were able to determine the physical properties of the perturbing material, i.e., mineral oil, on top of the B-G device. These two pieces of information show that KTP is useful for liquid sensing applications.

The sensitivity of the B-G acoustic wave sensing method was calculated using the equations described by B. A. Auld, "Acoustic Fields and Waves in Solids", Volume 2, Chapter 12, pages 271–281 (1973). The calculated sensitivity is $10^{-10}$ g/cm$^2$, which is very suitable for applications involving minute mass variations such as immunoassays and thin polymeric films.

EXAMPLE 3

Immunoassay for Detection of Rabbit Immunoglobulin (r-IgG)

This example demonstrates adsorption of antibody on the surface of both KTP and Lithium Niobate crystals. The antigen-antibody activity of adsorbed antibody is quantitatively compared to activity of antibody bound to control polystyrene surface. The example further demonstrates a sandwich enzyme immunoassay for quantitative detection of rabbit-IgG.

Crystal Treatment

KTP and Lithium niobate crystals were cut receptively into series of smaller crystals of ca. the same dimensions 10 mm×5 mm×0.81 mm and 10 mm×5 mm×0.52 mm and affording surface areas ca. 115 mm$^2$/crystal. The surfaces of the crystals were then cleaned by washing sequentially in laboratory detergent (Alconox), acetone and then by treatment in an ultrasonic bath containing a mixture of $H_2SO_4$ and "Nochormix" (Godax Laboratories, Inc.). Following treatment the crystals were thoroughly rinsed in deionized water, heated to 645° C. for two minutes, and then cooled to room temperature.

Antibody Adsorption

The crystals were then immersed in an antibody solution containing 0.25 mg/ml goat anti-r-IgG antibody (whole molecule) purchased form Sigma Chem. St. Louis, (No. R-2004) and then incubated at 4° C. for ca. 240 hrs. For the polystyrene controls, 50 ul/well of the above antibody solutions were then placed in Inter Med, Nuc-Immuno microtiter pate wells. Coated surface area was ca. 71 mm$^2$/well. The plates and crystals were then washed free of excess antibody by 4 successive washes with pH 7.5 TRIS Sample buffer (50 mM Tris(hydroxymethyl)aminomethane) hydrochloride buffer, sodium chloride (75 mM), 0.1% Poly-tergent SLF-18 surfactant (Olin Chemical, Stamford, Conn.). Prior to use the crystals were then stored immersed in 10 mM phosphate buffered (pH 7.4), 120 mM saline solution (PBS) at 4° C.

"Sandwich" r-IgG Immunoassay

The above antibody treated crystals were placed individually in 1.5 ml polypropylene plastic vials (Brinkmann Instruments Co., Westbury, N.Y.). Each crystal was then covered with 0.6 ml of a sample solution containing rabbit IgG antigen prepared in TRIS Sample buffer in concentrations 0, 0.05, 0.5 and 5.0 μg/ml. The crystals were then incubated with tumbling (12 rpm) for 30 min. at room temperature. Sample solutions were removed by aspiration and each crystal washed successively three times with 1.5 ml of TRIS sample buffer. Following antigen incubation, each crystal was then covered with 0.6 ml of an enzyme antibody reporter conjugate solution prepared by diluting monoclonal antirabbit IgG (whole molecule) alkaline phosphatase conjugate (Sigma Chemical Co., St. Louis, Mo.) 1:1000 in TRIS Sample buffer. The crystals were then incubated for 30 min. at room temperature with tumbling (12 rpm). Excess conjugate solution was removed and the individual crystals successively washed four time with 1.5 ml portion of TRIS Sample buffer. The crystals were then transferred to fresh polypropylene tubes and covered with 0.6 ml of p-nitrophenol substrate solution prepared by dissolving one 50-80-01 p-nitrophenol substrate tablet (Kiirkegarrd & Perry Laboratories) in a five fold dilution of KPL 50-80-02 phosphatase substrate concentrate (Kirkegaard & Perry Laboratories) diluted in de-ionized water. The crystals were then incubated at room temperature for 30 min. with tumbling (12 rpm). At 10, 20, and 30 minute intervals portions of the reaction solutions were removed and read spectrophotometrically at 405 nm.

In like manner as described above for treatment of KTP and Li Niobate test crystals, polystyrene microtiter plate wells were coated with the goat anti-r-IgG antibody as above. The test wells were then agitated at room temperature with 0.05 ml portions of the above sample antigen solutions containing rabbit IgG antigen concentrations of 0, 0.05, 0.5 and 5.0 μg/ml in TRIS Sample buffer. The test wells were then washed three times with TRIS sample buffer and incubated with agitation for 30 min. at room temperature with 0.32 ml of the above 1:1000 dilution of anti-r-IgG alkaline phosphatase conjugate reagent. The test wells were then freed of excess conjugate reagent by successively washing each well four times with excess TRIS sample buffer. p-Nitrophenol substrate solution, prepared as above, was then added and incubated with agitation at room temperature for 30 min. At various time intervals (0, 10, 20, 30 min.) portions of the substrate solutions were removed and read spectrophotometrically at 405 nm.

Figure 3:
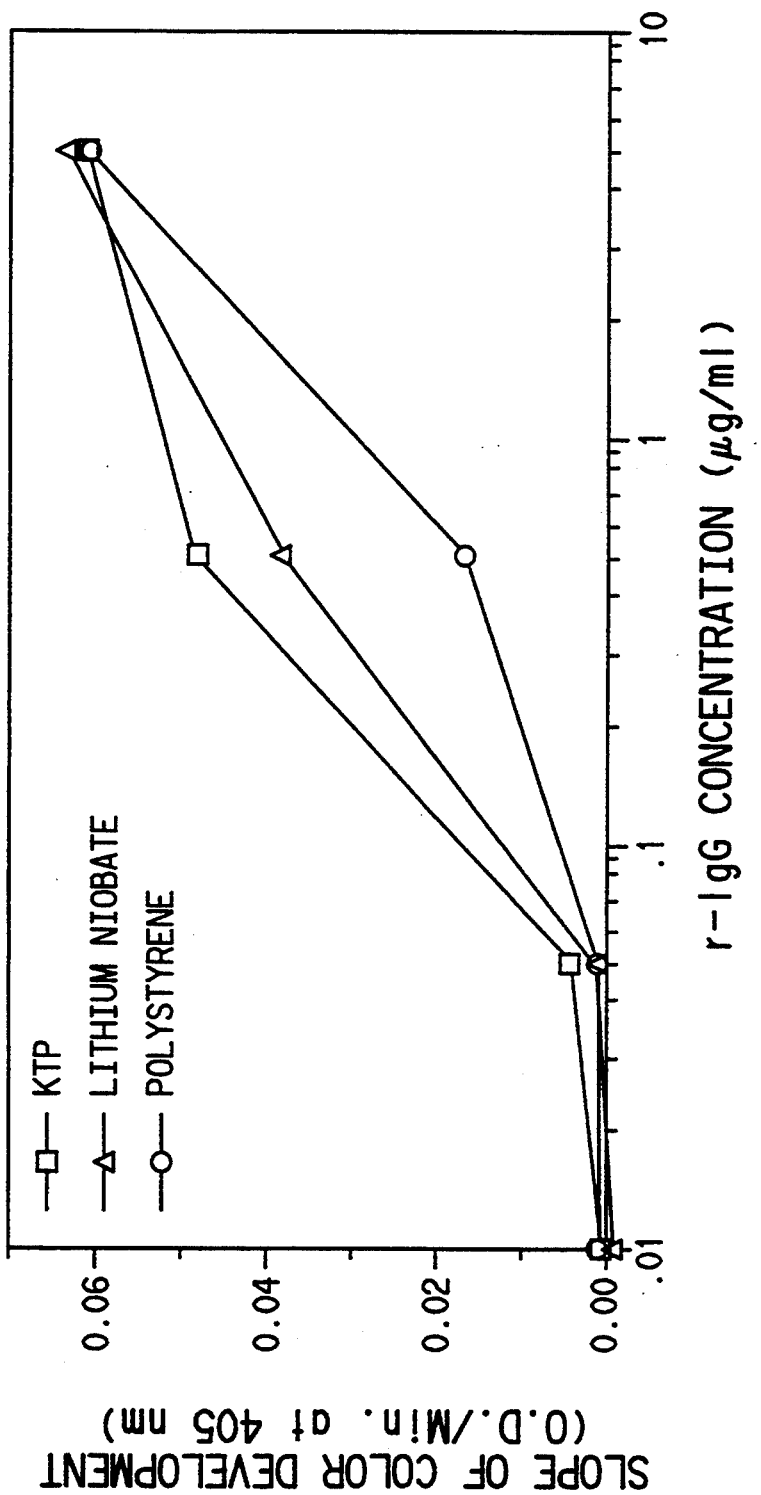
FIG. 3 is a graphical representation of an IgG antigen assay using KTP, lithium niobate, and polystyrene at various antigen concentrations.
Figure 4:
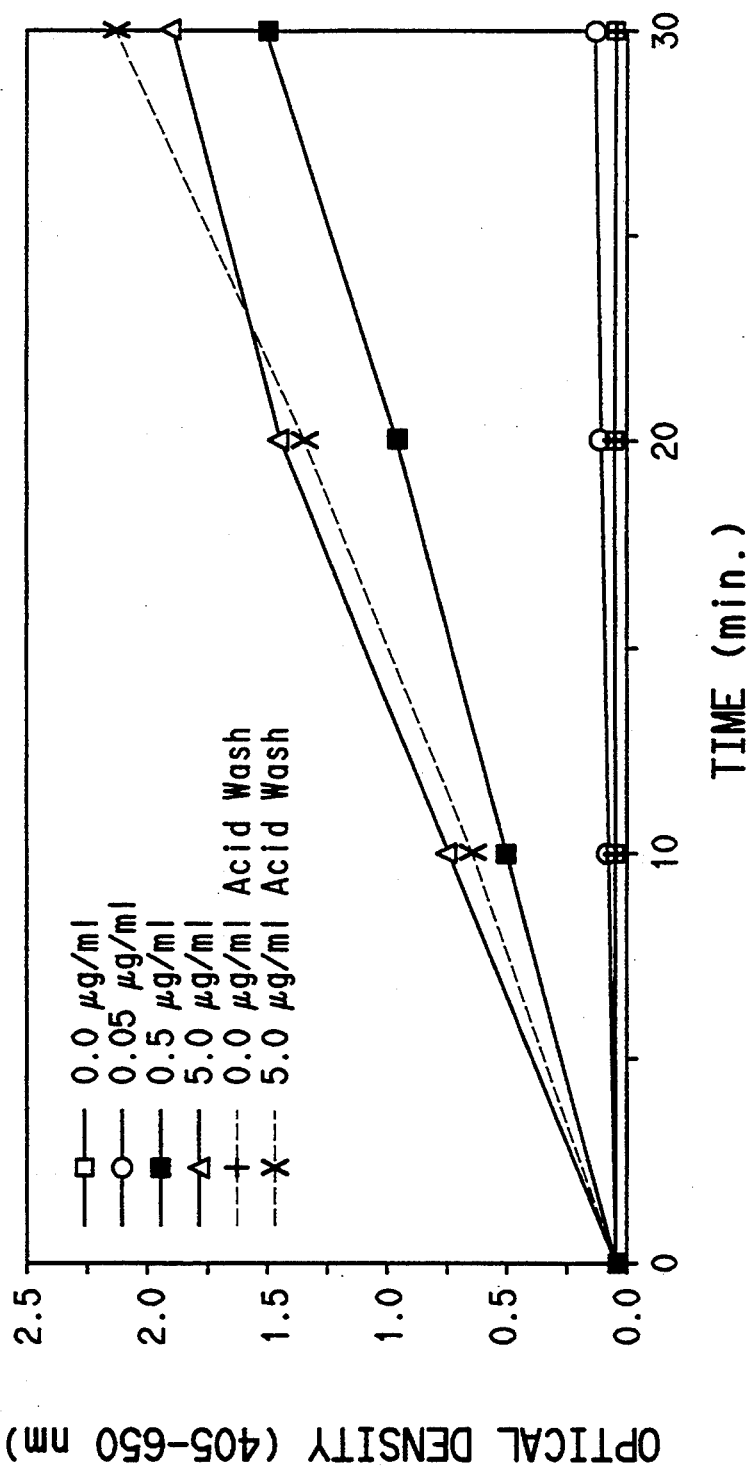
FIG. 4 is a graphical representation of a r-IgG assay response on KTP over time of signal generation.

Data are summarized in Table 1. The rates of color formation and thus enzymatic activities for each test material were measured by determining the rate of color formation from calculations of the slope of color formation with time (FIG. 4). This was determined at each test antigen (r-IgG) concentration and for each of the antibody coated KTP, Li Niobate and polystyrene test surfaces. The rate of color formation was first determined as a function of r-IgG concentration (FIG. 3). These data indicated that antibody bound to the surface of KTP and Li Niobate were active and capable of binding the test antigen r-IgG. Furthermore the antigen binding activities of KTP and Li Niobate were similar in amount to that of the polystyrene controls.

Data accumulated with samples containing no r-IgG, further indicated lower (>3 fold) non-specific reporter binding (NSB) for both KTP and Li Niobate-antibody supports than for the polystyrene control. These data demonstrate an important advantage of these materials; low blank rate, which is significant since assay sensitivity is ultimately dependent upon the signal to noise response of the specific assay.

TABLE 1

Data on Supports for Antibody Activity

| Material | Test # | Length (mm) | Width (mm) | Thickness (mm) | Approx Area (sq mm) | Concentration (μg/ml) |
|---|---|---|---|---|---|---|
| KTP | 1 | 10 | 5 | 0.81 | 115.62 | 0.00 |
| KTP | 2 | 10 | 5 | 0.81 | 115.62 | 0.05 |
| KTP | 3 | 10 | 5 | 0.81 | 115.62 | 0.50 |
| KTP | 4 | 10 | 5 | 0.81 | 115.62 | 5.00 |
| KTP | 5 | 10 | 5 | 0.81 | 115.62 | 0.00 Acid Wash |
| KTP | 6 | 10 | 5 | 0.81 | 115.62 | 5.00 Acid Wash |
| Lithium Niobate | 1 | 10 | 5 | 0.516 | 115.48 | 0.00 |
| Lithium Niobate | 2 | 10 | 5 | 0.516 | 115.48 | 0.05 |
| Lithium Niobate | 3 | 10 | 5 | 0.516 | 115.48 | 0.50 |
| Lithium Niobate | 4 | 10 | 5 | 0.516 | 115.48 | 5.00 |
| Lithium Niobate | 5 | 10 | 5 | 0.516 | 115.48 | 0.00 Acid Wash |
| Lithium Niobate | 6 | 10 | 5 | 0.516 | 115.48 | 5.00 Acid Wash |
| Polystyrene | | 6.94 dia. | No Width | Height of | 70.50 | 0.00 |
| Polystyrene | | 6.94 dia. | No Width | liquid in well. | 70.50 | 0.05 |
| Polystyrene | | 6.94 dia. | No Width | 1.5 | 70.50 | 0.50 |
| Polystyrene | | 6.94 dia. | No Width | | 70.50 | 5.00 |

| Material | 0 min (OD) | 10 min (OD) | 20 min (OD) | 30 min (OD) | Slope O.D./Min | Corr. Cof. |
|---|---|---|---|---|---|---|
| KTP | 0.048 | 0.049 | 0.053 | 0.058 | 0.000346 | 0.941 |
| KTP | 0.048 | 0.085 | 0.140 | 0.192 | 0.004876 | 0.994 |
| KTP | 0.048 | 0.491 | 0.928 | 1.521 | 0.048566 | 0.994 |
| KTP | 0.048 | 0.739 | 1.422 | 1.854 | 0.061010 | 0.990 |
| KTP | 0.048 | 0.047 | 0.049 | 0.053 | 0.000176 | 0.728 |
| KTP | 0.048 | 0.656 | 1.276 | 2.150 | 0.069266 | 0.991 |
| Lithium Niobate | 0.046 | 0.049 | 0.050 | 0.050 | 0.000130 | 0.786 |
| Lithium Niobate | 0.046 | 0.058 | 0.076 | 0.095 | 0.001650 | 0.990 |
| Lithium Niobate | 0.046 | 0.373 | 0.733 | 1.086 | 0.038000 | 1.000 |
| Lithium Niobate | 0.046 | 0.512 | 1.350 | 2.046 | 0.063800 | 0.989 |
| Lithium Niobate | 0.046 | 0.050 | 0.050 | 0.054 | 0.000240 | 0.900 |
| Lithium Niobate | 0.046 | 0.537 | 1.086 | 1.716 | 0.055590 | 0.997 |
| Polystyrene | 0.043 | 0.049 | 0.062 | 0.085 | 0.001390 | 0.930 |
| Polystyrene | 0.043 | 0.049 | 0.063 | 0.097 | 0.001760 | 0.884 |
| Polystyrene | 0.043 | 0.079 | 0.263 | 0.825 | 0.016930 | 0.903 |
| Polystyrene | 0.043 | 0.097 | 0.546 | 1.822 | 0.060470 | 0.893 |

Note: For KPT and Lithum Nibate, used 600 μl of Antigen and Substrate.
For Polystyrene used 325 μl of Antigen and Substrate.

What is claimed is:

1. A composition comprising:
   crystalline $MTiOXO_4$ having an analyte receptor immobilized on a surface of said crystalline $MTiOXO_4$;
   wherein M is selected from the group consisting of K, Rb, Tl, and $NH_4$, and X is P or As; provided that when M is $NH_4$, X is P.

2. The composition of claim 1, wherein M is K and X is P.

3. The composition of claim 1, wherein the analyte receptor is a bioreceptor.

4. The composition of claim 3, wherein the bioreceptor is immunoreactive.

5. The composition of claim 4, wherein the bioreceptor is an antibody.

6. The composition of claim 1, wherein the analyte receptor is immobilized directly to the crystalline $MTiOXO_4$.

7. The composition of claim 1, wherein the analyte receptor is immobilized to the crystalline $MTiOXO_4$ via an immobilization matrix.

8. A process for the detection of an analyte, comprising the step of:
   (a) immobilizing a receptor having specific binding affinity for said analyte onto a surface of crystalline $MTiOXO_4$,
   wherein M is selected from the group consisting of K, Rb, Tl, and $NH_4$; and X is P or As; provided that when M is $NH_4$, X is P;
   (b) contacting the surface of the crystalline $MTiOXO_4$ with a solution containing the analyte to be detected, whereby the analyte will bind to the immobilized receptor;
   (c) applying electromagnetic energy to the crystalline $MTiOXO_4$, whereby acoustic waves characterized by a frequency are generated; and
   (d) measuring the frequency of said acoustic waves; whereby by detecting a change in the frequency of said waves the presence of analyte is detected.

9. A process for the detection of an analyte, comprising the steps of:
   (a) immobilizing a receptor having specific binding affinity for said analyte onto a surface of crystalline $MTiOXO_4$,
   wherein M is selected from the group consisting of K, Rb, Tl, and $NH_4$; and X is P or As; provided that when M is $NH_4$, X is P;
   (b) contacting the surface of the crystalline $MTiOXO_4$ with a solution containing the analyte to be detected, whereby the analyte will bind to the immobilized receptor;
   (c) applying electromagnetic radiation to the crystalline $MTiOXO_4$; and
   (d) measuring the optical properties of the crystalline $MTiOXO_4$; whereby by detecting a change in said optical properties the presence of analyte is detected.

10. The process of claim 8 or 9, wherein M is K and X is P.

11. The process of claim 8 or 9, wherein the receptor is a bioreceptor.

12. The process of claim 8 or 9, wherein the bioreceptor is immunoreactive.

13. The process of claim 8 or 9, wherein the bioreceptor is a nucleic acid.

14. The process of claim 8 or 9, wherein the receptor is immobilizing directly onto the surface of the crystalline $MTiOXO_4$.

15. The process of claim 8 or 9, wherein the receptor is immobilized to the crystalline $MTiOXO_4$ via an immobilization matrix.

* * * * *